(12) United States Patent
Gu et al.

(10) Patent No.: US 11,534,398 B2
(45) Date of Patent: Dec. 27, 2022

(54) INHALED PREPARATION OF ISOGLYCYRRHIZIC ACID OR SALT THEREOF, AND USE IN PREPARING DRUGS FOR TREATING RESPIRATORY SYSTEM DISEASES

(71) Applicant: Chia Tai Tianqing Pharmaceutical Group Co., Ltd., Lianyungang (CN)

(72) Inventors: Hongmei Gu, Lianyungang (CN); Shanchun Wang, Lianyungang (CN); Xiquan Zhang, Lianyungang (CN); Lei Huang, Lianyungang (CN); Hongjiang Xu, Lianyungang (CN); Wei Song, Lianyungang (CN); Ping Dong, Lianyungang (CN); Zhongying Sun, Lianyungang (CN); Ying Zhang, Lianyungang (CN); Deyang Chen, Lianyungang (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 0 days.

(21) Appl. No.: 16/988,289

(22) Filed: Aug. 7, 2020

(65) Prior Publication Data
US 2020/0368158 A1 Nov. 26, 2020

Related U.S. Application Data

(63) Continuation of application No. 16/093,087, filed as application No. PCT/CN2017/080583 on Apr. 14, 2017, now abandoned.

(30) Foreign Application Priority Data

Apr. 15, 2016 (CN) .......................... 201610237175.3

(51) Int. Cl.
| | | |
|---|---|---|
| A61K 9/00 | (2006.01) | |
| A61K 31/704 | (2006.01) | |
| A61P 11/10 | (2006.01) | |
| A61K 47/02 | (2006.01) | |
| A61K 47/26 | (2006.01) | |
| A61P 11/00 | (2006.01) | |
| A61P 1/16 | (2006.01) | |
| A61P 31/12 | (2006.01) | |
| A61K 47/12 | (2006.01) | |
| A61K 47/24 | (2006.01) | |

(52) U.S. Cl.
CPC .......... *A61K 9/0078* (2013.01); *A61K 9/0075* (2013.01); *A61K 31/704* (2013.01); *A61K 47/02* (2013.01); *A61K 47/12* (2013.01); *A61K 47/24* (2013.01); *A61P 1/16* (2018.01); *A61P 11/00* (2018.01); *A61P 11/10* (2018.01); *A61P 31/12* (2018.01); *A61K 47/26* (2013.01)

(58) Field of Classification Search
CPC .......................... A61K 31/704; A61K 31/7016
See application file for complete search history.

(56) References Cited

U.S. PATENT DOCUMENTS

| 4,933,169 A | 6/1990 | Shanbrom |
|---|---|---|
| 9,642,799 B2 | 5/2017 | Broeckx et al. |
| 2007/0183983 A1 | 8/2007 | Morishita |

FOREIGN PATENT DOCUMENTS

| CN | 101023953 A | | 8/2007 |
|---|---|---|---|
| CN | 101190232 A | | 6/2008 |
| CN | 101396368 A | | 4/2009 |
| CN | 101669962 A | * | 3/2010 |
| CN | 101669962 A | | 3/2010 |
| CN | 102920936 A | | 2/2013 |
| CN | 103156930 A | | 6/2013 |
| CN | 104042573 A | | 9/2014 |
| CN | 106237297 A | * | 12/2016 |
| JP | 2008222682 A | * | 9/2008 |
| JP | 2009-513529 A | | 4/2009 |
| JP | 2015-509972 A | | 4/2015 |
| WO | WO 2005/004845 A1 | | 1/2005 |
| WO | WO 2005/004914 A1 | | 1/2005 |
| WO | WO 2012/026928 A1 | | 3/2012 |

OTHER PUBLICATIONS

Wong-Beringer, A. et al., Chest, "Suitability of Caspofungin for Aerosol Delivery", 2005, vol. 128, No. 5, pp. 3711-3716 (Year: 2005).*
Wang et al., CN101669962A English translation (Year: 2010).*
Yoichiro et al., JP2008222682A English translation (Year: 2008).*
Yin, Jinlong et al., CN106237297A Pharmaceutical composition for treating chronic bronchitis, machine translation, 6 pages (Year: 2016).*
Reagan-Shaw, S. et al., "Dose translation from animal to human studies revised," The FASEB Journal, vol. 22, pp. 659-661, 2007 (3 pages).
Zhang, M. et al.; "Effects of Licorice and its Extracts on Respiratory System"; Drugs & Clinic, vol. 25, No. 4, pp. 262-265; Apr. 30, 2010; ISSN: 1674-5516 (6 pages).
Ding N. et al.; "Research on the Comparison Between the Epimerides of 18 alpha-Glycyrrhizic Acid and 18 beta-Glycyrrhizic Acid"; Chinese J. Mod. Applied Pharmacy, vol. 28, No. 13, pp. 1312-1314; May 31, 2011; ISSN: 1007-7693 (5 pages).
Li, Y. et al.; "Clinical Application of Isoglycyrrhizinate Magnesium Injection"; Practical Pharmacy and Clinical Remedies, vol. 14, No. 6, pp. 521-522; Jun. 30, 2011 (2 pages).
International Search Report in International Application No. PCT/CN2017/080583, dated Jul. 19, 2017 (5 pages, w/English translation).

(Continued)

*Primary Examiner* — Bahar Craigo
(74) *Attorney, Agent, or Firm* — Nixon Peabody LLP

(57) ABSTRACT

The present invention belongs to the field of medicine, relates to an inhaled preparation of isoglycyrrhizic acid or a salt thereof, and in particular relates to an inhaled preparation of magnesium isoglycyrrhizinate and the use thereof in preparing drugs for treating respiratory system diseases.

10 Claims, No Drawings

(56) References Cited

OTHER PUBLICATIONS

Written Opinion in International Application No. PCT/CN2017/080583, dated Jul. 19, 2017 (3 pages) (English translation not available).

Extended European Search Report for European Patent Application No. 17781942.2, dated Oct. 21, 2019 (9 pages).

Kao, T-C. et al., "Glycyrrhizic Acid and 18β-Glycyrrhetinic Acid Inhibit Inflammation via PI3K/Akt/GSK3β Signaling and Glucocorticoid Receptor Activation," Journal of Agicultural and Food Chemistry 58, pp. 8623-8629 (2010).

Inthavong, K. et al., "Simulation of sprayed particle deposition in a human nasal cavity including a nasal spray device," Journal of Aerosol Science 42, 99. 100-113, 2011.

Weng, L.-L. et al., "The progress of the research on quality control and safety evaluation of inhalation preparations," Chin. J. Pharm. Anal., 33(5): 724-729, 2013.

Yamaguchi et al., "Inhalation Treatment," History of Medicine, pp. 246-249, 1991 (4 pages w/English abstract).

* cited by examiner

INHALED PREPARATION OF ISOGLYCYRRHIZIC ACID OR SALT THEREOF, AND USE IN PREPARING DRUGS FOR TREATING RESPIRATORY SYSTEM DISEASES

CROSS-REFERENCES TO RELATED APPLICATIONS

The present application is a continuation of U.S. patent application Ser. No. 16/093,087 filed Oct. 11, 2018; U.S. patent application Ser. No. 16/093,087 is a U.S. national phase of International Application No. PCT/CN2017/080583 filed Apr. 14, 2017, which claims priority to Chinese Application No. 201610237175.3, filed on Apr. 15, 2016, and all content thereof is incorporated by reference in its entirety into the text of this application.

FIELD OF THE INVENTION

The present invention belongs to the field of medicine, relates to an inhaled preparation of isoglycyrrhizic acid or a salt thereof, and in particular relates to an inhaled preparation of magnesium isoglycyrrhizinate and the use thereof in preparing drugs for treating respiratory system diseases.

BACKGROUND OF THE INVENTION

Glycyrrhiza is a commonly used medicinal plant, and main active ingredient thereof is glycyrrhizic acid species, namely 18-β glycyrrhizic acid and 18-α glycyrrhizic acid (also known as isoglycyrrhizic acid). Chinese patent ZL02111693.8 discloses a new compound magnesium isoglycyrrhizinate (structure shown in Formula I, with molecular weight of 845); proved by a large number of pharmacological and biochemical studies, it can obviously prevent transaminase elevation in animal serum, reduce the liver cell degeneration, necrosis and inflammatory cell infiltration, and promote hepatocyte regeneration in liver-injury animal models caused by different hepatotoxic agents (for example, acute liver injury in rats induced by D-galactosamine, chronic liver injury and liver cirrhosis in rats induced by carbon tetrachloride, and immune liver injury in black mice induced by Gal/FCA), and effect of magnesium isoglycyrrhizinate on resisting liver injury was obviously better than that of natural glycyrrhizic acid.

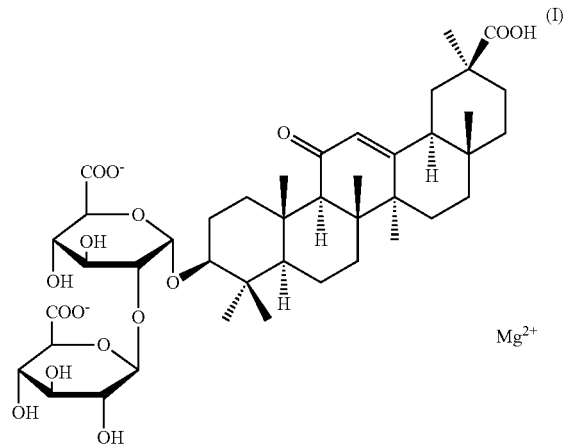

Glycyrrhiza has extensive pharmacological effects. In traditional Chinese medicine, glycyrrhiza and extracts thereof are considered to have many effects such as cardiotonic, eliminating phlegm, relieving cough, relieving asthma, pulmonary protection, broad-spectrum antibacterial and antiviral effect, etc. Researches in pharmacodynamics of the active ingredients thereof and new dosage forms have received considerable attention. Chinese patent ZL200410041923.8 discloses a magnesium isoglycyrrhizinate gel preparation and the use thereof in preparing drugs for treating psoriasis, chronic eczema dermatitis, contact dermatitis and other allergic skin diseases; Chinese patent ZL200510106108.X discloses a magnesium isoglycyrrhizinate preparation for intravenous and the use thereof in preparing drugs for treating liver disease; Chinese patent ZL200510106109.4 discloses an oral preparation of magnesium isoglycyrrhizinate and the use thereof in preparing drugs for treating liver disease, eczema, dermatitis, psoriasis and urticaria; Chinese patent ZL200510106110.7 discloses an external preparation of magnesium isoglycyrrhizinate and the use thereof in drugs for treating psoriasis, chronic eczema dermatitis, contact dermatitis and other allergic dermatological; Chinese patent ZL200610098077.2 discloses a lyophilized powder of magnesium isoglycyrrhizinate for injection and preparation method thereof.

Viral hepatitis is an infectious disease of hepatic pathological changes caused by various hepatitis viruses. Clinically, the main manifestations are loss of appetite, nausea, upper abdominal discomfort, liver pain, and fatigue. Some patients may have jaundice fever and liver enlargement accompanying with liver damage. Chronic viral hepatitis is the case in which the course of viral hepatitis lasts for half a year or more. Magnesium isoglycyrrhizinate is clinically suitable for treating chronic viral hepatitis and improving liver function abnormalities, but patient compliance is poor since it is administered intravenously. Sequential therapy, also known as "conversion therapy," is a new treatment proposed by American and European scholars in the 1980s, which refers to that when treating diseases by using drugs, parenteral administration (intravenous injection) is utilized in initial stage for 2 to 3 days, then changed to oral administration after the clinical symptoms is basically stable and improved. Although intravenous drip is used for the purpose of timely treatment for patients who cannot be administrated orally, it will inevitably lead to corresponding adverse reactions, such as infusion reaction, vascular stimulation and phlebitis, causing pain to the patients. Sequential therapy can shorten the time of intravenous administration and reduce the incidence of adverse reactions related to infusion, which can greatly shorten the hospitalization time of patients, save the expenses of individuals and medical institutions, save limited economic resources, and reduce the related social labor losses caused by hospitalization of patients. At present, the clinically recommended sequential therapy for chronic hepatitis is relatively simple, and commonly used method is intravenous infusion of magnesium isoglycyrrhizinate injection plus oral administration of diammonium glycyrrhizinate capsule. Since liver cells are not the only host cells of hepatitis virus, there exists a problem of low bioavailability when using diammonium glycyrrhizinate preparation to treat viral hepatitis, and it has to increase the dosage to achieve the desired therapeutic effect, but the risk of side effects of the drug is also increased at the same time. Therefore, there is an urgent need to find a better pharmaceutical preparation of magnesium isoglycyrrhizinate and to provide a sequential therapy for treating chronic viral hepatitis with high bioavailability.

Inhaled preparation means a preparation that delivers the drug by a specific device in the form of mist to the respiratory tract and/or lungs to exert a local or systemic effect. The properties of the drug itself also have a greater impact on the absorption process. Fine particle dose is an important parameter to evaluate the effectiveness of inhaled preparations. Controlling aerodynamic particle size of the powder, changing surface properties, and adjusting the type and size of the carrier can increase fine particle dose and pulmonary deposition ratio, thereby increasing bioavailability. As for dry powder inhaled preparation, if the drug particles are highly hygroscopic, aggregation, drug particle enlargement and stratification are very likely to occur during drug preparation and storage, thereby affecting the pulmonary deposition amount of the drug particles, and further affecting the efficacy. In addition, the drug with proper solubility in the respiratory system (such as respiratory secretion or alveolar fluid) is better absorbed; the absorption of the drug in the lung is passive diffusion, and the lipid-solubility of the drug molecule plays an important role therein. Most of the lipid-soluble drugs are absorbed by the bilayer lipid membrane of alveolar epithelial cells, so the drug with a larger oil/water partition coefficient could be absorbed more rapidly; the absorption effect of the drug in the lung is also related to the molecular weight, while most of small molecule drugs are absorbed through the pores of the alveolar epithelial cells, so that drugs with a smaller molecular weight are generally absorbed faster. The use of magnesium isoglycyrrhizinate prepared as an inhaled preparation for treating diseases has not been reported, and the molecular weight of magnesium isoglycyrrhizinate is moderate, thus preparing it into an inhaled preparation may present a great challenge.

Chronic obstructive pulmonary disease (COPD) is a common and frequently-occurring disease of the respiratory system, characterized in incompletely reversible and persistent airflow limitation. With the progressive development of airflow limitation, the chronic inflammatory response of the airway and lung caused by harmful particles or gases is increased, and acute exacerbations and complications often affect the severity of the overall disease of the patients. It is reported that the incidence and mortality of COPD are increasing year by year, and it is now the fourth leading cause of death in the world, seriously jeopardizing the health of the people, and has become an important public health problem due to its heavy social and economic burden. The onset of COPD can be manifested as a stable phase and an acute exacerbation phase. The treatment of COPD in a stable phase includes drug treatment and non-drug treatment. The main drug treatments are bronchodilators, glucocorticoids, expectorants (mucolytic agents), antioxidants, immunomodulators, vaccines, etc., and long-term regular inhaled glucocorticoids are more suitable for patients with severe COPD (grade III) and very severe COPD (grade IV) (FEV1<50% predicted); this treatment can reduce the frequency of acute exacerbation and improve quality of life. Non-drug treatment includes education and management, controlling occupational or environmental pollution, oxygen therapy, rehabilitation therapy and surgical treatment, while the purpose thereof is to relieve symptoms, improve health condition, enhance immunity, prevent disease progression, reduce the number of acute attacks, reduce mortality, improve activity endurance, and improve quality of life. However, researches have confirmed that the current treatment cannot alleviate the long-term decline tendency in lung function of patients with COPD, especially the effective prevention and treatment for the progressive decline of lung function in stable phase are lacked, and the long-term application of glucocorticoids and β2 receptor agonists inevitably bring some side effects, thus it is still necessary to find better drugs and preparations for the treatment of COPD.

Cough, phlegm and asthma are the three common symptoms of the respiratory system, which are present simultaneously and interact with each other, which not only bring pain to the patients, but also is life threatening. Expectorant is a drug that can make the sputum thinning, reduce the viscosity and make it easy to cough up. At the same time, it accelerates the mucociliary movement of the respiratory mucosa, improves the sputum transport function, weakens the stimulation to the respiratory mucosa, indirectly relieves cough and asthma, and is beneficial for controlling secondary infections.

With the increasing application of aerosolizing inhalation therapy in respiratory system diseases, especially in expelling phlegm and treating common diseases such as asthma, COPD and the like, the market of inhaled preparation has a broad prospect. At present, the use of glycyrrhizic acid inhaled preparations in preparing drugs for expelling phlegm and treating chronic obstructive pulmonary disease has not been reported.

SUMMARY OF THE INVENTION

In one aspect, the present invention provides an inhaled preparation of isoglycyrrhizic acid or a salt thereof.

In one embodiment of the present invention, the salt is magnesium salt, ammonium salt, potassium salt, sodium salt or salt of various amino acids, preferably magnesium salt, ammonium salt, potassium salt or sodium salt. More preferably, it is magnesium salt.

In one embodiment of the present invention, the inhaled preparation is selected from inhalation aerosol, powder for inhalation, liquid preparation for use in nebulizers, and preparation that can be converted into vapor. Preferably, the inhaled preparation is selected from powder for inhalation or liquid preparation for use in nebulizers.

In a preferred embodiment of the present invention, the inhaled preparation of the invention is powder for inhalation, comprising: micronized magnesium isoglycyrrhizinate and one or more pharmaceutically acceptable carriers, wherein the particle size of micronized magnesium isoglycyrrhizinate is 0.5-10 µm. Preferably, the particle size of micronized magnesium isoglycyrrhizinate is 0.5-5 µm.

"The particle size of magnesium isoglycyrrhizinate is 0.5-10 µm" as used in the present invention means that the particle size of most magnesium isoglycyrrhizinate (Active Pharmaceutical Ingredient, API) is in the range of 0.5-10 µm, and further, the particle size distribution of magnesium isoglycyrrhizinate is limited to $X_{10} \geq 0.5$ µm, $X_{80} \leq 10$ µm. The "$X_{10}$" in the present invention refers to a particle size with distribution of 10%, that is, the volume content of particles with a particle size smaller than that accounts for 10% of the total particles; "$X_{50}$" refers to a particle size with distribution of 50%, that is, the volume content of particles with a particle size smaller than that accounts for 50% of the total particles; "$X_{80}$" refers to a particle size with distribution of 80%, that is, the volume content of particles with a particle size smaller than that accounts for 80% of the total particles; "$X_{90}$" refers to a particle size with distribution of 90%, that is, the volume content of particles with a particle size smaller than that accounts for 90% of the total particles.

The "pharmaceutically acceptable carrier" according to the present invention is selected from lactose, mannitol, trehalose or glycine, preferably lactose, further preferably ground lactose, sieved lactose or a mixture of sieved lactose and fine lactose, wherein the particle size distribution of ground lactose ranges from 1 µm to 350 µm, preferably with the particle size distribution of $X_{50}$<30-110 µm; the particle size distribution of sieved lactose ranges from 1 µm to 200 µm, preferably with the particle size distribution of $X_{50}$<35-115 µm; the particle size distribution of fine lactose ranges from 1 µm to 60 µm, preferably with the particle size distribution of $X_{90}$<45 µm.

The term "ground lactose" as used in the present invention refers to lactose which is mechanically ground to different degrees of fineness, and the particle size distribution varies depending on different grades of ground lactose; specifically, the particle size distribution ranges from 1 µm to 350 µm, with the particle size distribution of $X_{50}$<30-110 µm. The term "sieved lactose" as used in the present invention refers to lactose which could have a relatively narrow particle size distribution by sieving; specifically, the particle size distribution thereof ranges from 1 µm to 200 µm, with the particle size distribution of $X_{50}$<35-115 µm. The "fine lactose" as used in the present invention includes micronized fine lactose and finely ground lactose with a narrow particle size distribution; specifically, the particle size distribution of fine lactose ranges from 1 µm to 60 µm, with the particle size distribution of $X_{90}$<45 µm.

In one embodiment of the present invention, the above micronized magnesium isoglycyrrhizinate and carriers are mixed and filled into a capsule or a bubble-cap. In a further embodiment, each capsule or bubble-cap comprises 1-50 mg of micronized magnesium isoglycyrrhizinate and 0-50 mg of lactose. Preferably, each capsule or bubble-cap comprises 1-30 mg of micronized magnesium isoglycyrrhizinate and 1-40 mg of lactose.

In another preferred embodiment of the present invention, the powder for inhalation of the present invention further comprises one or more pharmaceutically acceptable additives.

The "pharmaceutically acceptable additive" as used in the present invention includes one or more selected from surfactants, lubricants, and flavoring agents.

In some embodiments of the present invention, the pharmaceutically acceptable additive is surfactant, such as phospholipid, poloxamer.

In some embodiments of the present invention, the pharmaceutically acceptable additive is lubricant, such as magnesium stearate, micronized silica gel, talcum powder.

In some embodiments of the present invention, the pharmaceutically acceptable additive is flavoring agent, including natural flavoring agents and synthetic flavors. Natural flavoring agent is such as peppermint oil, orange peel oil, cinnamon oil, spearmint oil, mint water, compound orange spirit; synthetic flavor is such as banana flavor, pineapple flavor, and orange flavor.

In another preferred embodiment of the present invention, the inhaled preparation of the present invention is a liquid preparation for use in nebulizers, comprising magnesium isoglycyrrhizinate, isotonicity adjusting agent, pH adjusting agent and water for injection, with pH of 6.0-8.0; the nebulizer is a continuous nebulizer or a quantitative nebulizer.

In a preferred embodiment of the present invention, the amount of magnesium isoglycyrrhizinate is from 0.1 mg/ml to 5 mg/ml, preferably from 0.1 mg/ml to 2.5 mg/ml. In some embodiments, the amount of magnesium isoglycyrrhizinate is from 0.1 mg/ml to 0.5 mg/ml. In some embodiments, the amount of magnesium isoglycyrrhizinate is from 0.5 mg/ml to 2.5 mg/ml.

In a preferred embodiment of the present invention, the isotonicity adjusting agent is one or more selected from glucose, sodium chloride, potassium chloride, mannitol, preferably sodium chloride.

In a preferred embodiment of the present invention, the pH adjusting agent is one or more selected from sodium hydroxide, ammonium hydroxide, hydrochloric acid, sodium carbonate, sodium bicarbonate, dilute sulfuric acid, citric acid, sodium citrate, acetic acid, tartaric acid, sodium acetate or disodium hydrogen phosphate, preferably ammonium hydroxide or sodium hydroxide.

In a preferred embodiment of the present invention, the pH is 6.5-7.0.

Preferably, the liquid preparation for use in nebulizers is provided in the form of a single dose package, and the single dose package size is 1 ml, 2 ml or 5 ml. It is preferably 2 ml.

In some embodiments of the present invention, the inhaled preparation is a liquid preparation for use in nebulizers provided in a multi-dose package, and the multi-dose package size is 10 ml, 20 ml or 30 ml.

In some embodiments of the present invention, the liquid preparation for use in nebulizers comprises flavoring agent, including natural flavoring agents and synthetic flavors. Natural flavoring agent is such as peppermint oil, orange peel oil, cinnamon oil, spearmint oil, mint water, compound orange spirit; synthetic flavor is such as banana flavor, pineapple flavor, and orange flavor.

One object of the present invention is to provide a dosing regimen for an inhaled preparation of isoglycyrrhizic acid or a salt thereof, wherein said regimen comprises that the administration frequency of said inhaled preparation to a subject is selected from: up to three times a day, up to twice a day, up to once a day, and up to once every other day, preferably up to twice a day.

In another aspect, the present invention provides the use of inhaled preparation of isoglycyrrhizic acid or a salt thereof in preparing drugs for treating chronic viral hepatitis. Preferably, the isoglycyrrhizic acid or a salt thereof is selected from magnesium isoglycyrrhizinate.

In another aspect, the present invention provides the use of inhaled preparation of magnesium isoglycyrrhizinate in preparing drugs for treating chronic viral hepatitis by sequential therapy, wherein magnesium isoglycyrrhizinate injection and magnesium isoglycyrrhizinate inhaled preparation are used in the sequential therapy.

In a further aspect, the present invention provides a combination comprising magnesium isoglycyrrhizinate inhaled preparation and magnesium isoglycyrrhizinate injection.

In another aspect, the invention provides a method for treating chronic viral hepatitis, comprising administering a therapeutically effective amount of inhaled preparation of isoglycyrrhizic acid or a salt thereof to a patient with chronic viral hepatitis. In some embodiments, the inhaled preparation is selected from inhalation aerosol, powder for inhalation, liquid preparation for use in nebulizers, and preparation that can be converted into vapor. Preferably, the inhaled preparation is selected from powder for inhalation or liquid preparation for use in nebulizers.

In a further aspect, the invention provides a kit, comprising an inhaled preparation of isoglycyrrhizic acid or a salt thereof in a package containing one or more single doses, a drug delivery device, an instruction, and a suitable package. In some embodiments, the inhaled preparation is selected from inhalation aerosol, powder for inhalation, liquid preparation for use in nebulizers, and preparation that can be converted into vapor. Preferably, the inhaled preparation is selected from powder for inhalation or liquid preparation for use in nebulizers. In some embodiments, the drug delivery device of the liquid preparation for use in nebulizers is a nebulizer, which is a continuous nebulizer or a quantitative nebulizer. In some embodiments, the instruction relates to a method for treating chronic viral hepatitis, comprising administering a therapeutically effective amount of inhaled preparation of isoglycyrrhizic acid or a salt thereof to a patient with chronic viral hepatitis.

In still another aspect, the present invention provides the use of inhaled preparation of isoglycyrrhizic acid or a salt thereof in preparing drugs for treating chronic obstructive pulmonary disease. Preferably, the isoglycyrrhizic acid or a salt thereof is selected from magnesium isoglycyrrhizinate.

In one embodiment of the present invention, the inhaled preparation is selected from inhalation aerosol, powder for inhalation, liquid preparation for use in nebulizers, and preparation that can be converted into vapor. Preferably, the inhaled preparation is selected from powder for inhalation or liquid preparation for use in nebulizers; most preferably, the inhaled preparation is selected from liquid preparation for use in nebulizers.

In a preferred embodiment of the present invention, the inhaled preparation of the present invention is a liquid preparation for use in nebulizers, comprising magnesium isoglycyrrhizinate, isotonicity adjusting agent, pH adjusting agent, and water for injection, with the pH of 6.0-8.0, and the nebulizer is a continuous nebulizer or a quantitative nebulizer.

In a preferred embodiment of the present invention, the amount of magnesium isoglycyrrhizinate is from 0.1 mg/ml to 5 mg/ml, preferably from 0.1 mg/ml to 2.5 mg/ml. In some embodiments, the amount of magnesium isoglycyrrhizinate is from 0.1 mg/ml to 0.5 mg/ml. In some embodiments, the amount of magnesium isoglycyrrhizinate is from 0.5 mg/ml to 2.5 mg/ml.

In a preferred embodiment of the present invention, the isotonicity adjusting agent is one or more selected from glucose, sodium chloride, potassium chloride, mannitol, preferably sodium chloride.

In a preferred embodiment of the present invention, the pH adjusting agent is one or more selected from sodium hydroxide, ammonium hydroxide, hydrochloric acid, sodium carbonate, sodium bicarbonate, dilute sulfuric acid, citric acid, sodium citrate, acetic acid, tartaric acid, sodium acetate or disodium hydrogen phosphate, preferably ammonium hydroxide or sodium hydroxide.

In a preferred embodiment of the present invention, the pH is 6.5-7.0.

Preferably, the liquid preparation for use in nebulizers is provided in the form of a single dose package, and the single dose package size is 1 ml, 2 ml or 5 ml. It is preferably 2 ml.

In some embodiments of the present invention, the inhaled preparation is provided as a liquid preparation for use in nebulizers in the form of a multi-dose package, and the multi-dose package size is 10 ml, 20 ml or 30 ml.

In some embodiments of the present invention, the liquid preparation for use in nebulizers comprises flavoring agent, including natural flavoring agent and synthetic flavor. Natural flavoring agent is such as peppermint oil, orange peel oil, cinnamon oil, spearmint oil, mint water, compound orange spirit; synthetic flavor is such as banana flavor, pineapple flavor, and orange flavor.

In one embodiment of the present invention, the administration frequency of said inhaled preparation to a subject is selected from: up to three times a day, up to twice a day, up to once a day, and up to once every other day, preferably up to twice a day.

In a preferred embodiment of the present invention, in an animal model in which COPD in rats was induced by cigarette smoke inhalation, the pharmacological effects of the magnesium isoglycyrrhizinate inhaled preparation are evaluated by using trachea administration or aerosolization of the magnesium isoglycyrrhizinate inhaled preparation.

In a preferred embodiment of the present invention, in an animal model in which COPD in mice was induced by lipopolysaccharide (LPS), the pharmacological effects of the magnesium isoglycyrrhizinate inhaled preparation are evaluated by aerosolization of the magnesium isoglycyrrhizinate inhaled preparation once a day and twice a day, with the dosage divided into three doses, namely low dose, medium dose and high dose (respectively 0.5 mg/ml, 1.5 mg/ml and 5 mg/ml).

In another aspect, the present invention provides a method for treating chronic obstructive pulmonary disease, comprising administering a therapeutically effective amount of inhaled preparation of isoglycyrrhizic acid or a salt thereof to a patient with chronic obstructive pulmonary disease. In some embodiments, the inhaled preparation is selected from inhalation aerosol, powder for inhalation, liquid preparation for use in nebulizers, and preparation that can be converted into vapor. Preferably, the inhaled preparation is selected from powder for inhalation or liquid preparation for use in nebulizers; most preferably, the inhaled preparation is selected from liquid preparation for use in nebulizers. In some embodiments, the administration frequency of the inhaled preparation to the subject is selected from: up to three times a day, up to twice a day, up to once a day, and up to once every other day, preferably up to twice a day.

In a further aspect, the invention provides a kit, comprising an inhaled preparation of isoglycyrrhizic acid or a salt thereof in a package containing one or more single doses, a drug delivery device, an instruction, and a suitable package. In some embodiments, the inhaled preparation is selected from inhalation aerosol, powder for inhalation, liquid preparation for use in nebulizers, and preparation that can be converted into vapor. Preferably, the inhaled preparation is selected from powder for inhalation or liquid preparation for use in nebulizers; and most preferably, the inhaled preparation is selected from liquid preparation for use in nebulizers. In some embodiments, the drug delivery device of the liquid preparation for use in nebulizers is a nebulizer, which is a continuous nebulizer or a quantitative nebulizer. In some embodiments, the instruction relates to a method for treating chronic obstructive pulmonary disease, comprising administering a therapeutically effective amount of inhaled preparation of isoglycyrrhizic acid or a salt thereof to a patient with chronic obstructive pulmonary disease.

In still another aspect, the present invention provides the use of inhaled preparation of isoglycyrrhetic acid or a salt thereof in preparing expectorant, wherein the expectorant is a drug that can make the sputum thinning, reduce the viscosity and make it easy to cough up. Preferably, the isoglycyrrhizic acid or a salt thereof is selected from magnesium isoglycyrrhizinate.

In an embodiment of the present invention, the inhaled preparation is selected from inhalation aerosol, powder for inhalation, liquid preparation for use in nebulizers, and preparation that can be converted into vapor. Preferably, the inhaled preparation is selected from powder for inhalation or liquid preparation for use in nebulizers; most preferably, the inhaled preparation is selected from a liquid preparation for use in nebulizers.

In a preferred embodiment of the present invention, the inhaled preparation of the present invention is a liquid preparation for use in nebulizers, comprising: magnesium isoglycyrrhizinate, isotonicity adjusting agent, pH adjusting agent, and water for injection, with the pH of 6.0-8.0, and the nebulizer is a continuous nebulizer or a quantitative nebulizer.

In a preferred embodiment of the present invention, the amount of magnesium isoglycyrrhizinate is from 0.1 mg/ml to 5 mg/ml, preferably from 0.2 mg/ml to 2.5 mg/ml. In some embodiments, the amount of magnesium isoglycyrrhizinate is from 0.2 mg/ml to 0.5 mg/ml. In some embodiments, the amount of magnesium isoglycyrrhizinate is from 0.5 mg/ml to 2.5 mg/ml.

In a preferred embodiment of the present invention, the isotonicity adjusting agent is onre or more selected from glucose, sodium chloride, potassium chloride, mannitol, preferably sodium chloride.

In a preferred embodiment of the present invention, the pH adjusting agent is one or more selected from sodium hydroxide, ammonium hydroxide, hydrochloric acid, sodium carbonate, sodium bicarbonate, dilute sulfuric acid, citric acid, sodium citrate, acetic acid, tartaric acid, sodium acetate or disodium hydrogen phosphate, preferably ammonium hydroxide or sodium hydroxide.

In a preferred embodiment of the present invention, the pH is 6.5-7.0.

Preferably, the liquid preparation for use in nebulizers is provided in the form of a single dose package, and the single dose package size is 1 ml, 2 ml or 5 ml. It is preferably 2 ml.

In some embodiments of the present invention, the inhaled preparation is provided as a liquid preparation for use in nebulizers in the form of a multi-dose package, and the multi-dose package size is 10 ml, 20 ml or 30 ml.

In some embodiments of the present invention, the liquid preparation for use in nebulizers comprises flavoring agent, including natural flavoring agent and synthetic flavor. Natural flavoring agent is such as peppermint oil, orange peel oil, cinnamon oil, spearmint oil, mint water, compound orange spirit; synthetic flavor is such as banana flavor, pineapple flavor, and orange flavor.

In a preferred embodiment of the present invention, the mouse phenol red excretion assay is used to evaluate the effect of magnesium isoglycyrrhizinate inhaled preparation on tracheal secretion of mice.

In another aspect, the present invention provides a method for expelling phlegm, comprising administering a therapeutically effective amount of an inhaled preparation of isoglycyrrhizic acid or a salt thereof to a patient having abnormal sputum secretion and/or dysfunction of sputum. In some embodiments, the inhaled preparation is selected from inhalation aerosol, powder for inhalation, liquid preparation for use in nebulizers, and preparation that can be converted into vapor. Preferably, the inhaled preparation is selected from powder for inhalation or liquid preparation for use in nebulizers; most preferably, the inhaled preparation is selected from a liquid preparation for use in nebulizers.

In a further aspect, the invention provides a kit, comprising an inhaled preparation of isoglycyrrhizic acid or a salt thereof in a package containing one or more single doses, a drug delivery device, an instruction, and a suitable package. In some embodiments, the inhaled preparation is selected from inhalation aerosol, powder for inhalation, liquid preparation for use in nebulizers, and preparation that can be converted into vapor. Preferably, the inhaled preparation is selected from powder for inhalation or liquid preparation for use in nebulizers; and most preferably, the inhaled preparation is selected from liquid preparation for use in nebulizers. In some embodiments, the drug delivery device of the liquid preparation for use in nebulizers is a nebulizer, which is a continuous nebulizer or a quantitative nebulizer. In some embodiments, the instruction relates to a method for expelling phlegm, comprising administering a therapeutically effective amount of inhaled preparation of isoglycyrrhizic acid or a salt thereof to a patient having abnormal sputum secretion, dysfunction of sputum.

The chemical name of the term "isoglycyrrhizic acid" is: (18α,20β)-20-carboxy-11-oxo-30-norolean-12-ene-3β-yl-2-O-β-D-pyranoglucuronyl-α-D-pyranoglucuronic acid.

The chemical name of the term "magnesium isoglycyrrhizinate" is: magnesium (18α,20β)-20-carboxy-11-oxo-30-norolean-12-ene-3β-yl-2-O-β-D-pyranoglucuronyl-α-D-pyranoglucuronate, the structure thereof shown in Formula I. The term further includes hydrates thereof, such as tetrahydrate.

The inventors unexpectedly discovered that the magnesium isoglycyrrhizinate with medium molecular weight can be prepared into an inhaled preparation, which has a high emptying rate and a high fine particle fraction, and inhalation administration can make magnesium isoglycyrrhizinate rapidly enter the bloodstream in the lung, thereby entering the blood circulation to play a systemic role. Compared with common oral preparations, the bioavailability of magnesium isoglycyrrhizinate inhaled preparation is significantly improved, thereby the dosage and the risk of toxic side effects can be reduced; compared with the injection, the bioavailability of the magnesium isoglycyrrhizinate inhaled preparation is equivalent, but that makes the patient actively or passively receive inhaled preparation, which greatly reduces the pain caused by injection and improves patient compliance. Therefore, the inhaled preparation of the present invention is extremely suitable for sequential use with an injection solution, and the pain and treatment costs brought by injection are reduced while ensuring the efficacy.

In the animal model of chronic obstructive pulmonary disease in rats induced by cigarette smoke inhalation, magnesium isoglycyrrhizinate inhaled preparation can alleviate the clinical symptoms of COPD rats, inhibit the infiltration of neutrophils-based inflammatory factors in COPD rats, significantly reduce lung inflammation, improve the role of the bronchial wall, reduce bronchial mucus secretion and improve emphysema, while the experiment proved that it has significant effect on the treatment of COPD. At the same time, different ways of administration of magnesium isoglycyrrhizinate vary the efficacy, and that of the aerosolizing inhalation route (0.4 mg/ml of the magnesium isoglycyrrhizinate liquid preparation for use in nebulizers, 30 min) has the most significantly effect on reducing inflammation.

In the animal model of chronic obstructive pulmonary disease in mice induced by lipopolysaccharide (LPS), compared with the model group, each dose group of magnesium isoglycyrrhizinate inhaled preparation significantly lowers the number of white blood cells in the bronchial airway of mice. In the case of administrating magnesium isoglycyrrhizinate inhaled preparation in the form of liquid prepara tion for use in nebulizers twice a day, the therapeutic effect of the low dose and medium dose groups are comparable to that of the positive control group, and the therapeutic effect of the high dose group is slightly weaker than that of the low dose and medium dose groups. In addition, the therapeutic effect of administrating magnesium isoglycyrrhizinate twice a day is better than that of once a day at the same dose.

The mouse phenol red excretion method is used to evaluate the effect of magnesium isoglycyrrhizinate inhaled preparation on the tracheal secretion of mice, and it is found that the phenol red excretion of aerosolization administration for 15 min (0.2 mg/ml of the magnesium isoglycyrrhizinate liquid preparation for use in nebulizers) is significantly increased compared with the control group ($p<0.01$).

DETAILED EMBODIMENTS OF THE INVENTION

The present invention will be further illustrated below in conjunction with specific examples. It should be understood that these examples are provided for illustrative purposes only and are not intended to limit the scope of the present invention.

The assay methods which do not specify the specific conditions in the following examples may be carried out according to conventional conditions or according to the conditions recommended by the manufacturer. Unless otherwise defined, all technical and scientific terms used herein have the same meaning known as those skilled in the art.

EXAMPLES

Example 1

Magnesium Isoglycyrrhizinate Powder for Inhalation

The magnesium isoglycyrrhizinate was micronized to obtain samples having the following different particle size ranges.

| Particle size of the active ingredient | $X_{10}/\mu m$ | $X_{50}/\mu m$ | $X_{90}/\mu m$ |
|---|---|---|---|
| Large particle size | 1.47 | 5.75 | 17.24 |
| Medium particle size | 1.38 | 5.08 | 12.64 |
| Small particle size | 0.58 | 2.03 | 5.69 |

Example 1a

Prescription:

| | |
|---|---|
| Magnesium isoglycyrrhizinate (large particle size) | 1 g |
| Lactose A | 2 g |
| Amount of preparation | 100 capsules |

Preparation Process:
1) The prescribed amount of magnesium isoglycyrrhizinate and the prescribed amount of lactose were taken;
2) Then sieved and mixed;
3) The capsules were filled according to 30 mg/capsule, and each capsule contained 10 mg of magnesium isoglycyrrhizinate;
4) The key quality indicators of powder for inhalation were detected according to requirements of general rule 0111 in the fourth part of the "Chinese Pharmacopoeia".

Example 1b

Prescription:

| | |
|---|---|
| Magnesium isoglycyrrhizinate (medium particle size) | 1 g |
| Lactose A | 2 g |
| Amount of preparation | 100 capsules |

Preparation Process:
1) The prescribed amount of magnesium isoglycyrrhizinate and the prescribed amount of lactose were taken;
2) Then sieved and mixed;
3) The capsules were filled according to 30 mg/capsule, and each capsule contained 10 mg of magnesium isoglycyrrhizinate;
4) The key quality indicators of powder for inhalation were detected according to requirements of general rule 0111 in the fourth part of the "Chinese Pharmacopoeia".

Example 1c

Prescription:

| | |
|---|---|
| Magnesium isoglycyrrhizinate (small particle size) | 1 g |
| Lactose A | 2 g |
| Amount of preparation | 100 capsules |

Preparation Process:
1) The prescribed amount of magnesium isoglycyrrhizinate and the prescribed amount of lactose were taken;
2) Then sieved and mixed;
3) The capsules were filled according to 30 mg/capsule, and each capsule contained 10 mg of magnesium isoglycyrrhizinate;
4) The key quality indicators of powder for inhalation were detected according to requirements of general rule 0111 in the fourth part of the "Chinese Pharmacopoeia".

Comparison of key quality indicators:

| Quality indicator | Example 1a | Example 1b | Example 1c |
|---|---|---|---|
| Emptying rate | 99% | 99% | 99% |
| Fine particle fraction | 13% | 20% | 32% |

The fine particle dose was an important parameter to evaluate the effectiveness of the inhaled preparation. The particle size of the magnesium isoglycyrrhizinate had a crucial influence on the fine particle fraction as the key quality indicator of the powder for inhalation. Therefore, the particle size of the magnesium isoglycyrrhizinate was controlled within the range of 0.5-10 μm. The fine particle fraction was >15%, in line with regulations of the pharmacopoeia.

Example 2

Magnesium Isoglycyrrhizinate Powder for Inhalation

The effects of lactose with different types and different sizes on the key quality indicators of magnesium isoglycyrrhizinate powder for inhalation were compared.

| Lactose type | Description | particle size/μm |
|---|---|---|
| Lactose A | sieved lactose with a narrow particle size distribution | $X_{10}$: 30-60; $X_{50}$: 70-110; $X_{90}$: 110-150 |
| Lactose B | | $X_{10}$: 7-22; $X_{50}$: 40-70; $X_{90}$: 80-120 |
| Lactose C | ground lactose with the average particle size being strictly controlled | $X_{10}$: 5-15; $X_{50}$: 50-100; $X_{90}$: 120-160 |
| Lactose D | ground lactose with a wide particle size distribution | 40%-60% < 45; 75%-100% < 100; 90%-100% < 150; 99.5%-100% < 315 |
| Lactose E | finely ground lactose with a narrow particle size distribution | 90%-100% < 45; 98%-100% < 63; 100% < 150 |
| Lactose F | micronized fine lactose | $X_{50}$ < 5; $X_{90}$ < 10 |

Note:
a typical particle size range of lactose D is: $X_{10}$: 1-10 μm; $X_{50}$: 30-50 μm; $X_{90}$: 70-150 μm.

Example 2a

Prescription:

| | |
|---|---|
| Magnesium isoglycyrrhizinate (small particle size) | 1 g |
| Lactose B | 2 g |
| Amount of preparation | 100 capsules |

Preparation Process:

1) The prescribed amount of magnesium isoglycyrrhizinate and the prescribed amount of lactose were taken;

2) Then sieved and mixed;

3) The capsules were filled according to 30 mg/capsule, and each capsule contained 10 mg of magnesium isoglycyrrhizinate;

4) The key quality indicators of powder for inhalation were detected according to requirements of general rule 0111 in the fourth part of the "Chinese Pharmacopoeia".

Example 2b

Prescription:

| | |
|---|---|
| Magnesium isoglycyrrhizinate (small particle size) | 1 g |
| Lactose C | 2 g |
| Amount of preparation | 100 capsules |

Preparation Process:

1) The prescribed amount of magnesium isoglycyrrhizinate and the prescribed amount of lactose were taken;

2) Then sieved and mixed;

3) The capsules were filled according to 30 mg/capsule, and each capsule contained 10 mg of magnesium isoglycyrrhizinate;

4) The key quality indicators of powder for inhalation were detected according to requirements of general rule 0111 in the fourth part of the "Chinese Pharmacopoeia".

Example 2c

Prescription:

| | |
|---|---|
| Magnesium isoglycyrrhizinate (small particle size) | 1 g |
| Lactose D | 2 g |
| Amount of preparation | 100 capsules |

Preparation Process:

1) The prescribed amount of magnesium isoglycyrrhizinate and the prescribed amount of lactose were taken;

2) Then sieved and mixed;

3) The capsules were filled according to 30 mg/capsule, and each capsule contained 10 mg of magnesium isoglycyrrhizinate;

4) The key quality indicators of powder for inhalation were detected according to requirements of general rule 0111 in the fourth part of the "Chinese Pharmacopoeia".

Example 2d

Prescription:

| | |
|---|---|
| Magnesium isoglycyrrhizinate (small particle size) | 1 g |
| Lactose E | 2 g |
| Amount of preparation | 100 capsules |

Preparation Process:

1) The prescribed amount of magnesium isoglycyrrhizinate and the prescribed amount of lactose were taken;

2) Then sieved and mixed;

3) The capsules were filled according to 30 mg/capsule, and each capsule contained 10 mg of magnesium isoglycyrrhizinate;

4) The key quality indicators of powder for inhalation were detected according to requirements of general rule 0111 in the fourth part of the "Chinese Pharmacopoeia".

Example 2e

Prescription:

| | |
|---|---|
| Magnesium isoglycyrrhizinate (small particle size) | 1 g |
| Lactose A | 1.5 g |
| Lactose F | 0.5 g |
| Amount of preparation | 100 capsules |

Preparation Process:

1) The prescribed amount of magnesium isoglycyrrhizinate and the prescribed amount of lactose were taken;

2) Then sieved and mixed;

3) The capsules were filled according to 30 mg/capsule, and each capsule contained 10 mg of magnesium isoglycyrrhizinate;

4) The key quality indicators of powder for inhalation were detected according to requirements of general rule 0111 in the fourth part of the "Chinese Pharmacopoeia".

Example 2f

Prescription:

| | |
|---|---|
| Magnesium isoglycyrrhizinate (small particle size) | 1 g |
| Lactose B | 1.5 g |

-continued

| | |
|---|---|
| Lactose F | 0.5 g |
| Amount of preparation | 100 capsules |

Preparation Process:

1) The prescribed amount of magnesium isoglycyrrhizinate and the prescribed amount of lactose were taken;
2) Then sieved and mixed;
3) The capsules were filled according to 30 mg/capsule, and each capsule contained 10 mg of magnesium isoglycyrrhizinate;
4) The key quality indicators of powder for inhalation were detected according to requirements of general rule 0111 in the fourth part of the "Chinese Pharmacopoeia".

Comparison of key quality indicators:

| Quality Indicators | Example 2a | Example 2b | Example 2c | Example 2d | Example 2e | Example 2f |
|---|---|---|---|---|---|---|
| Emptying rate | 99% | 97% | 97% | 90% | 97% | 98% |
| Fine particle fraction | 35% | 40% | 46% | 48% | 43% | 45% |

Different types and different particle sizes of lactose had crucial influence on the key quality indicators of powder for inhalation. The fine particle fraction in the sample prepared by sieved lactose alone with the active ingredient was lower, but the fine particle fraction could be significantly improved when adding a certain amount of fine lactose when preparing the sample. The fine particle fraction of the sample prepared by ground lactose and the active ingredient was higher.

Example 3

Magnesium Isoglycyrrhizinate Liquid Preparation for Use in Nebulizers Prescription

| | |
|---|---|
| Magnesium isoglycyrrhizinate | 10 g |
| Sodium chloride | 18 g |
| Ammonium hydroxide | q.s. |
| Water for injection | to 2000 ml |
| Amount of preparation | 1000 preparations |

Preparation Process:

The prescribed amount of magnesium isoglycyrrhizinate and sodium chloride were taken and added into 1800 ml of water for injection, stirred until completely dissolved. Then ammonium hydroxide was added to adjust the pH value of the solution to 6.5-7.0, and the obtained solution was added with water for injection to 2000 ml, filtered and sterilized, filled according to 2 ml per package, before a liquid preparation for use in nebulizers containing 10 mg of magnesium isoglycyrrhizinate was obtained.

Main Technical Evaluation Indicators:

| Time point | 0 day | Acceleration for 1 month | Acceleration for 2 months | Acceleration for 3 months | Long term for 3 months |
|---|---|---|---|---|---|
| Fne particle fraction | 38% | 38% | 39% | 37% | 38% |

Example 4

Magnesium Isoglycyrrhizinate Liquid Preparation for Use in Nebulizers Prescription

| | |
|---|---|
| Magnesium isoglycyrrhizinate | 5 g |
| Sodium chloride | 18 g |
| Ammonium hydroxide | q.s. |
| Water for injection | to 2000 ml |
| Amount of preparation | 1000 preparations |

Preparation Process:

The prescribed amount of magnesium isoglycyrrhizinate and sodium chloride were taken and added into 1800 ml of water for injection, stirred until completely dissolved. Then ammonium hydroxide was added to adjust the pH value of the solution to 6.5-7.0, and the obtained solution was added with water for injection to 2000 ml, filtered and sterilized, filled according to 2 ml per package, before a liquid preparation for use in nebulizer containing 5 mg of magnesium isoglycyrrhizinate was obtained.

Main Technical Evaluation Indicators:

| | Time point | | | | |
|---|---|---|---|---|---|
| | 0 day | Acceleration for 1 month | Acceleration for 2 months | Acceleration for 3 months | Long term for 3 months |
| Fine particle fraction | 39% | 38% | 36% | 37% | 40% |

Example 5

Magnesium Isoglycyrrhizinate Liquid Preparation for Use in Nebulizers

Prescription:

| | |
|---|---|
| Magnesium isoglycyrrhizinate | 1 g |
| Sodium chloride | 18 g |
| Ammonium hydroxide | q.s. |
| Water for injection | to 2000 ml |
| Amount of preparation | 1000 preparations |

Preparation Process:

The prescribed amount of magnesium isoglycyrrhizinate and sodium chloride were taken and added into 1800 ml of water for injection, stirred until completely dissolved. Then ammonium hydroxide was added to adjust the pH value of the solution to 6.5-7.0, and the obtained solution was added with water for injection to 2000 ml, filtered and sterilized, filled according to 2 ml per package, before a liquid preparation for use in nebulizer containing 1 mg of magnesium isoglycyrrhizinate was obtained.

Main Technical Evaluation Indicators:

| | Time point | | | | |
|---|---|---|---|---|---|
| | 0 day | Acceleration for 1 month | Acceleration for 2 months | Acceleration for 3 months | Long term for 3 months |
| Fine particle fraction | 42% | 38% | 39% | 39% | 40% |

Example 6

Magnesium Isoglycyrrhizinate Liquid Preparation for Use in Nebulizers Prescription

| | |
|---|---|
| Magnesium isoglycyrrhizinate | 0.4 g |
| Sodium chloride | 18 g |
| Ammonium hydroxide | q.s. |
| Water for injection | to 2000 ml |
| Amount of preparation | 1000 preparations |

Preparation Process:

The prescribed amount of magnesium isoglycyrrhizinate and sodium chloride were taken and added into 1800 ml of water for injection, stirred until completely dissolved. Then ammonium hydroxide was added to adjust the pH value of the solution to 6.5-7.0, and the obtained solution was added with water for injection to 2000 ml, filtered and sterilized, filled according to 2 ml per package, before a liquid preparation for use in nebulizer containing 0.4 mg of magnesium isoglycyrrhizinate was obtained.

Main Technical Evaluation Indicators:

| | Time point | | | | |
|---|---|---|---|---|---|
| | 0 day | Acceleration for 1 month | Acceleration for 2 months | Acceleration for 3 months | Long term for 3 months |
| Fine particle fraction | 40% | 39% | 37% | 41% | 38% |

Example 7

Magnesium Isoglycyrrhizinate Liquid Preparation for Use in Nebulizers Prescription

| | |
|---|---|
| Magnesium isoglycyrrhizinate | 0.2 g |
| Sodium chloride | 18 g |
| Ammonium hydroxide | q.s. |
| Water for injection | to 2000 ml |
| Amount of preparation | 1000 preparations |

Preparation Process:

The prescribed amount of magnesium isoglycyrrhizinate and sodium chloride were taken and added into 1800 ml of water for injection, stirred until completely dissolved. Then ammonium hydroxide was added to adjust the pH value of the solution to 6.5-7.0, and the obtained solution was added with water for injection to 2000 ml, filtered and sterilized, filled according to 2 ml per package, before a liquid preparation for use in nebulizer containing 0.2 mg of magnesium isoglycyrrhizinate was obtained.

Main Technical Evaluation Indicators:

| | Time point | | | | |
|---|---|---|---|---|---|
| | 0 day | Acceleration for 1 month | Acceleration for 2 months | Acceleration for 3 months | Long term for 3 months |
| Fine particle fraction | 40% | 43% | 42% | 39% | 40% |

Example 8

Pharmacokinetic Evaluation After Inhalation/Intragastric Administration to Rats Eight healthy male SD rats, weighing 223-252 g, were fed with standard formula granule feed of rats on time every day. The rats were fasted for 16 h before the experiment, and were refeeded at 4 h after the administration. Drinking water was free before, after and during the experiment. The rats were randomly divided into two groups, 4 rats in each group, and each rat was inhalation administrated with a single dose of magnesium isoglycyrrhizinate liquid preparation for use in nebulizers (2.5 mg/mL) and intragastric administrated with magnesium isoglycyrrhizinate inhaled preparation (5.0 mg/mL, the amount of isoglycyrrhizic acid is 4.486 mg/mL) respectively. Each rat in the inhalation administration group was given 200 μL of magnesium isoglycyrrhizinate liquid preparation for use in nebulizers (the actual dose given to the rat was 2.24-2.49 mg/kg). The dose in the intragastric administration group was 10.0 mg/kg. 0.2-0.3 mL of blood was taken from the fundus venous plexus before administration (0 h) and 0.0833 h, 0.25 h, 0.5 h, 1 h, 2 h, 4 h, 6 h, 8 h, 10 h, 24 h after administration. EDTA-K2 was used for anticoagulation, and the plasma was centrifuged. Then 50 μL was accurately measured, added with 10 μL internal standard solution to vortex and mixed, then added with 200 μL methanol, and mixed in high speed vortex mixer for 3 min, centrifuged for 10 min (4° C., 13000 rpm). The supernatant was collected, and 100 μL thereof was transferred to a 96-well plate. 50 μL of ultrapure water was added, vortexed, LC-MS/MS was used for detection, and the chromatogram was recorded.

The pharmacokinetic results of inhalation administration of the magnesium isoglycyrrhizinate liquid preparation for use in nebulizers and the intragastric administration of isoglycyrrhizic acid injection were as follows:

| PK parameters | Group Inhalation Sample size N = 4 | | | Intragastric N = 4 | | |
|---|---|---|---|---|---|---|
| | Mean | SD | RSD % | Mean | SD | RSD % |
| Dose (mg/kg) | 2.4 | 0.1 | | 10 | 0 | |
| Cmax (μg/L) | 3113 | 712 | 22.9% | 27.3 | 17.2 | 63.0% |
| AUC(0-t) (μg*h/L) | 14567 | 6427 | 44.1% | 89.8 | 105 | 118% |
| AUC(0-∞) (μg*h/L) | 14593 | 6427 | 44.0% | 102 | 102 | 100% |
| MRT(0-t) (h) | 3.52 | 1.09 | 31.0% | 2.35 | 1.58 | 67.1% |
| t½ z(h) | 2.13 | 0.69 | 32.3% | 1.88 | 1.47 | 78.4% |
| Tmax (h) | 0.81 | 0.80 | 98.5% | 1.75 | 2.84 | 162% |
| CLz/F (L/h/kg) | 0.195 | 0.103 | 53.0% | 162 | 90.1 | 55.7% |
| Cmax/Dose | 1315 | 306 | 23.3% | 2.73 | 1.72 | 63.0% |
| AUC(0-t)/Dose | 6108 | 2577 | 42.2% | 8.98 | 10.5 | 118% |
| relative F % | 68052% | | | | | |

In addition, the pharmacokinetic parameters of inhalation administration were compared with the average pharmacokinetic parameters of intravenous administration reported in the literature, and the results were as follows:

| | Group | |
|---|---|---|
| | Inhalation (N = 4) | Intravenous (N = 6) |
| Dose (mg/kg ) | 2.37 ± 0.13 | 30.0 |
| Cmax (μg/L) | 3113 ± 712 | 354500 |
| AUC(0-t) (μg*h/L) | 14567 ± 6427 | 209591 |
| AUC(0-∞) (μg*h/L) | 14593 ± 6427 | 212295 |
| MRT(0-t) (h) | 3.52 ± 1.09 | 1.71 |
| t1/2 z(h) | 2.13 ± 0.69 | 2.06 |
| Tmax(h) | 0.81 ± 0.8 | 0.0833 |
| CLz/F(L/h/kg) | 0.195 ± 0.103 | 141.3 |
| Cmax/Dose | 1315 ± 306 | 11817 |
| AUC(0-t)/Dose | 6108 ± 2577 | 6986 |
| Relative F % | 87% | |

Compared with intragastric administration, the relative bioavailability of magnesium isoglycyrrhizinate by inhalation administration for rats was as high as 68052%. Compared with intravenous administration, the bioavailability of magnesium isoglycyrrhizinate by inhalation administration for rats was 87%. Therefore, inhalation administration can significantly improve the bioavailability of magnesium isoglycyrrhizinate by compared with gastrointestinal administration, and the bioavailability of magnesium isoglycyrrhizinate by inhalation administration was basically equal to that by gastrointestinal administration.

Example 9

Pharmacodynamic Experiment of Magnesium Isoglycyrrhizinate Inhaled Preparation for Rats with Chronic Obstructive Pulmonary Disease 9.1 Experimental Method:

After modeling chronic obstructive pulmonary disease model induced by cigarette smoke inhalation, male SD rats were randomly divided into 6 groups according to the body weight: high dose tracheal instillation group (1.67 mg/ml of magnesium isoglycyrrhizinate, 100 μl/rat), low dose tracheal instillation group (1.67 mg/ml, 25 μl/rat), aerosolizing inhalation group, model group and blank control group, 10 rats in each group. During the intervention period, except that the control group and the model group were given normal saline, the other groups were successive administered every day, lasted for 15 days. During the administration period, the administration groups continued to be given with smoke stimulation after 30 minutes of administration, and the mental state, breathing, activity, hair luster, weight gain of the rats were recorded every day. 12 hour after the last administration, whole blood was taken from the rat eye for determination of white blood cell count and cell classified comparison. The rats were killed, the trachea and lungs were exposed by thoracotomy, and the morphology of the lungs and trachea was observed with the naked eye. The right lung was ligated at the right main branch, and the left lung was lavaged with normal saline 2 ml×3 times. The recovery rate was about 80%. The bronchoalveolar lavage fluid (BALF) was prepared for the determination of white blood cell count and classified comparison (white blood cells, neutrophils, lymphocytes and monocytes). Finally, the right lung of rat was fixed with 10% formalin and HE stained, lung injury was observed under microscope, and pathological lesions were scored. All scores were accumulated, and the average score of each animal in each group was calculated (mean±SD).

Scoring indicators: (1) whether there was mucus and cell blockage in the small airway cavity; (2) whether the small airway epithelium had necrotic erosion; (3) small airway epithelial cells goblet cell metaplasia; (4) small airway epithelial cell squamous metaplasia; (5) small airway wall inflammation cell infiltration; (6) small airway wall fibrous connective tissue hyperplasia; (7) small airway wall smooth muscle hyperplasia; (8) small airway wall pigmentation; and (9) lung emphysema. Lesion score: according to the degree from light to heavy lesions, it was quantified as slight or very small amount for "0.5 point", mild or small amount for "1 point", moderate or more quantity amount for "2 points", severe or plenty amount for "3 points", very severe or large amount for "4 points", and no obvious lesions for 0 point.

9.2 Experimental Results:

The experimental result data was expressed in the form of mean±SD. One-way ANOVA combined with Post-Hoc (LSD method) was used to analyze the differences between groups. Statistical significance was expressed as a P value of less than 0.05. The model group was compared with the blank control group, #p<0.05, #p<0.01; each administration group of magnesium isoglycyrrhizinate was compared with the model group, *p<0.05, **p<0.01.

9.2.1 Effect of Magnesium Isoglycyrrhizinate Inhaled Preparation on Body Weight of COPD Rats The experimental results (Table 1) showed that after the successful modeling of COPD, the weight gain of the rats in each administration group was slow compared with that in the blank control group, and there existed a significant difference when compared with that in the blank control group (p<0.01). After 16 days of administration, compared with the model group, the weight of the rats in the high dose tracheal instillation group, low dose tracheal instillation group and the aerosolizing inhalation group of magnesium isoglycyrrhizinate increased slowly, wherein the weight gain of the aerosolizing inhalation group was more, and each group still differed from that in the blank control group (p<0.01).

of magnesium isoglycyrrhizinate and nebulization, the symptoms of the rats in each group were relieved compared with the model group, wherein the magnesium isoglycyrrhizinate aerosolizing inhalation group was much more obvious than the other groups.

9.2.3 Effect of Magnesium Isoglycyrrhizinate Inhaled Preparation on the White Blood Cells Count and Cell Classified Comparison in COPD Rats The experimental results (Table 2) showed that the number of neutrophils and the percentage of neutrophils in the blood of rats in model group were increased to different degrees, and showed significant difference (p<0.05 or p<0.01). The above suggested that COPD rats had an inflammatory response mainly characterized by neutrophil infiltration after modeling. From the pharmacological point of view: high dose tracheal infusion group, low dose tracheal

TABLE 1 effect of magnesium isoglycyrrhizinate on body weight of COPD rats

| Group | Dose | Number of animals | Initial weight | End weight |
|---|---|---|---|---|
| Blank control group | 0.9% NS | 5 | 395.40 ± 16.50 | 460.60 ± 22.68 |
| Model group | 0.9% NS | 10 | 316.30 ± 20.06## | 343.00 ± 22.93## |
| High dose tracheal instillation group | 1.67 mg/ml, 100 μl | 10 | 324.6 ± 12.22** | 358.20 ± 16.17** |
| Low dose tracheal instillation group | 1.67 mg/ml, 25 μl | 10 | 317.60 ± 24.23** | 350.80 ± 27.79** |
| Aerosolizing inhalation group | 0.4 mg/ml, 30 min | 9 | 319.22 ± 10.43** | 360.11 ± 18.84** |

9.2.2 Effect of Magnesium Isoglycyrrhizinate Inhalation Preparation on General Symptoms of COPD Rats The experimental results showed that the rats in the blank control group had normal activities, sensitive reactions, body fat, and no symptoms such as cough, sneezing and dyspnea. After the model group was modeled, the rats tended to be prone, lack of spirit, stagnation, squint, bunching, unsteady walking, weight gain slowing, and grayish yellow fur, followed by symptoms such as cough, sneezing and dyspnea. After high dose and low dose tracheal infusion infusion group and aerosolizing inhalation group can significantly inhibit inflammatory factors mainly of neutrophils and percentage thereof in the blood of COPD rats, and the effect was obvious (p<0.05 or p<0.01). The effect of magnesium isoglycyrrhizinate in the aerosolizing inhalation group was the best (0.4 mg/ml, 30 min). The drug efficacy comparison was: magnesium isoglycyrrhizinate aerosolizing inhalation group>high dose tracheal instillation group>low dose tracheal instillation group.

TABLE 2

Effect of magnesium isoglycyrrhizinate on the white blood cell count and cell classified comparison in blood of COPD rats

| | | | (mean ± SD ) | | |
| Group | Dose | Number of animals | White blood cell count (10/μl) | Neutrophil count (10/μl) | Percentage of neutrophils (%) |
|---|---|---|---|---|---|
| Blank control group | — | 5 | 1399.00 ± 167.15 | 130.33 ± 14.01 | 9.40 ± 1.97 |
| Model group | — | 10 | 1277.50 ± 141.21 | 208.50 ± 44.83# | 16.39 ± 3.63# |
| High dose tracheal instillation group | 1.67 mg/ml, 100 μl | 10 | 1395.13 ± 270.32 | 153.25 ± 40.12* | 11.31 ± 3.55* |
| Low dose tracheal instillation group | 1.67 mg/ml, 25 μl | 10 | 1135.13 ± 155.73 | 155.13 ± 26.25* | 13.80 ± 2.24* |
| Aerosolizing inhalation group | 0.4 mg/ml, 30 min | 9 | 1123.33 ± 170.54 | 123.67 ± 23.24** | 11.05 ± 1.61** |

9.2.4 Effect of Magnesium Isoglycyrrhizinate Inhaled Preparation on the White Blood Cell Count and Cell Classified Comparison in BALF of COPD Rats The experimental results (Table 3) showed that the numbers of white blood cells and neutrophils, as well as percentage of neutrophils in the BALF of rats in the model group were increased to different degrees ($p<0.05$ or $p<0.01$). The above suggested that the lungs of COPD rats had an inflammatory response mainly characterized by neutrophil infiltration. From the drug efficacy point of view: the magnesium isoglycyrrhizinate aerosolizing inhalation group can reduce the number of neutrophils and the percentage thereof.

TABLE 3

Effect of magnesium isoglycyrrhizinate on the white blood cell count and cell classified comparison in BALF of COPD rats

| Group | Dose | Number of animals | White blood cell count (10/µl) (mean ± SD) | Neutrophil count (10/µl) (mean ± SD) | Percentage of neutrophils (%) (mean ± SD) |
|---|---|---|---|---|---|
| Blank control group | — | 5 | 55.67 ± 9.87 | 21.67 ± 5.69 | 38.57 ± 3.59 |
| Model group | — | 10 | 155.38 ± 31.99$^{\#\#}$ | 62.38 ± 27.62$^{\#}$ | 39.18 ± 12.36 |
| High dose tracheal instillation group | 1.67 mg/ml, 100 µl | 10 | 184.38 ± 32.15 | 89.88 ± 21.57* | 48.89 ± 9.69 |
| Low dose tracheal instillation group | 1.67 mg/ml, 25 µl | 10 | 172.50 ± 26.52 | 66.38 ± 25.46 | 38.08 ± 12.86 |
| Aerosolizing inhalation group | 0.4 mg/ml, 30 min | 9 | 170.33 ± 55.17 | 57.83 ± 20.78 | 38.83 ± 21.02 |

9.2.5 Effect of Magnesium Isoglycyrrhizinate Inhaled Preparation on Pathology of COPD Rats The experimental results (Table 4) showed that the lung tissue of rats in the blank control group consisted of alveolus, intrapulmonary bronchial branches and interstitial tissues with clear structure, no emphysema, minimal infiltration of inflammatory cells and goblet cell hyperplasia. The main lesions in the lung tissue of rats in the model group were interstitial pneumonia, edema around the perivascular tissue, with infiltration of inflammatory cells, increased goblet cells in the bronchial wall of the lung, degeneration and necrosis of bronchial wall cells, and a small amount of exudate in the bronchial lumen, wherein emphysema and inflammatory cell infiltration were particularly evident ($p<0.01$ or $p<0.05$). High dose tracheal infusion group, low dose tracheal infusion group and magnesium isoglycyrrhizinate aerosolizing inhalation group can significantly reduce lung inflammation, improve bronchial wall function, reduce bronchial mucus secretion and improve emphysema. Among them, magnesium isoglycyrrhizinate aerosolizing inhalation group (0.4 mg/ml, 30 min) was the most obvious to reduce inflammation and infiltration.

TABLE 4

Effect of magnesium isoglycyrrhizinate on pathology of COPD rats

| Group | Dose | Number of animals | Comprehensive score | Emphysema | Inflammatory cell infiltration | Bronchial mucus secretion |
|---|---|---|---|---|---|---|
| | | | Pathological score (mean ± SD) | | | |
| Blank control group | — | 5 | 0.50 ± 0.60 | 0.000 ± 0.000 | 0.200 ± 0.274 | 0.100 ± 0.224 |
| Model group | — | 10 | 2.20 ± 0.80$^{\#\#}$ | 0.450 ± 0.369$^{\#}$ | 1.100 ± 0.615** | 0.550 ± 0.438 |
| High dose tracheal instillation group | 1.67 mg/ml, 100 µl | 10 | 0.90 ± 0.52* | 0.300 ± 0.422 | 0.450 ± 0.550* | 0.050 ± 0.158** |
| Low dose tracheal instillation group | 1.67 mg/ml, 25 µl | 10 | 0.80 ± 0.50* | 0.150 ± 0.337 | 0.400 ± 0.394** | 0.200 ± 0.350 |
| Aerosolizing inhalation group | 0.4 mg/ml, 30 min | 9 | 0.89 ± 0.65* | 0.222 ± 0.441 | 0.389 ± 0.333** | 0.278 ± 0.363 |

Example 10

Pharmacodynamic Experiment of Magnesium Isoglycyrrhizinate Inhaled Preparation for Mice with Chronic Obstructive Pulmonary Disease

10.1 Experimental Method:

90 ICR male mice, weighing 18-22 g, were divided into 9 groups, including blank control group, model group, low dose group (0.5 mg/ml, q.d.), medium dose group (1.5 mg/ml, q.d.), high dose group (5.0 mg/ml, q.d.), low dose group (0.5 mg/ml, b.i.d.), medium dose group (1.5 mg/ml, b.i.d.), high dose group (5.0 mg/ml, b.i.d.) of magnesium isoglycyrrhizinate inhaled preparation and positive control (Arformoterol) group. After the anesthesia of the mice, the trachea thereof was instilled with 30 μl the lipopolysaccharide (LPS) to model. After modeling for 30 minutes, 10 ml of the drug was administered by nebulizing inhalation device, and the nebulizing time was 30 min. 6 hours after LPS modeling, low dose group (0.5 mg/ml, b.i.d.), medium dose group (1.5 mg/ml, b.i.d.), high dose group (5.0 mg/ml, b.i.d.) and positive control group were continually administrated with 10 ml of drugs by nebulizing inhalation device. 24 hours after modeling, the mice were anesthetized and lung tissues thereof were lavaged. The bronchoalveolar lavage fluid (BALF) was taken to measure the number of inflammatory cells. Some lung tissues were taken for HE staining and the pathological section was used to detect the changes of inflammatory cells.

TABLE 5-1

Effects of lipopolysaccharide on inflammatory cells (WBC) in the bronchial airways

| Group | WBC (109/L) | Upward ratio (%) |
|---|---|---|
| Blank control group | 0.1350 ± 0.0778 | — |
| Model group | 0.7971 ± 0.1931 | 490.48 |

TABLE 5-2

Effect of magnesium isoglycyrrhizinate inhaled preparation on inflammatory cells (WBC) in bronchial airways

| Group | WBC (109/L) | Downward ratio (%) |
|---|---|---|
| Model group | 0.7971 ± 0.1931 | — |
| Positive control group b.i.d. | 0.5310 ± 0.1424 | 33.39 |
| Low dose group b.i.d. | 0.5644 ± 0.1599 | 29.19 |
| Medium dose group b.i.d. | 0.5350 ± 0.1277 | 32.89 |
| High dose group b.i.d. | 0.6710 ± 0.1723 | 15.82 |
| Low dose group q.d. | 0.6511 ± 0.2319 | 18.32 |
| Medium dose group q.d. | 0.6622 ± 0.1895 | 16.93 |
| High dose group q.d. | 0.6730 ± 0.1665 | 15.57 |

10.2 Experimental Results:

The experimental results (Table 5-1) showed that a large number of inflammatory cells (white blood cells, WBC) were produced in the bronchial airway of the mice in the lipopolysaccharide-induced model group, which was up-regulated 490% compared with that in the blank control group, showing the successful induction of COPD. The histopathological examination of the lung tissue structure of the mice indicated that the model group showed obvious inflammatory reaction, the inflammatory cell infiltration was obvious, the exuded inflammatory cells were found in the alveolar and connective tissues of the alveolar septum. In particular, the neutrophils were arrested and aggregated obviously around the pulmonary blood vessels and all level of the bronchial tubes.

The experimental results (Table 5-2) showed that in the model test of lipopolysaccharide-induced COPD mice, the number of white blood cells in each dose group of magnesium isoglycyrrhizinate inhaled preparation was significantly different from that of the model group. Among them, the therapeutic effects of the low dose group (down-regulated WBC of 29%) and the medium dose group (down-regulated WBC of 33%) of the magnesium isoglycyrrhizinate inhaled preparation administrating twice a day were comparable to that of the positive control group (down-regulated WBC of 33%), and the therapeutic effect of high dose group was slightly weaker than those of low dose group and medium dose group. The effect of magnesium isoglycyrrhizinate administrated twice a day was better than once a day at the same dose. In addition, histopathological examination showed that no obvious inflammatory reaction was observed in each dose group of magnesium isoglycyrrhizinate inhaled preparation.

Example 11

Effect of Magnesium Isoglycyrrhizinate Inhaled Preparation on Airway Secretion

11.1 Experimental Method 50 male ICR mice, weighing about 21 g, were randomly divided into 5 groups: control group 1 (normal saline, NS), control group 2 (normal saline, NS), positive control group (ammonium chloride, 1 g/kg), drug group 1 (0.2 mg/ml of magnesium isoglycyrrhizinate liquid preparation for use in nebulizers, nebulizing for 30 min), drug group 2 (0.2 mg/ml of magnesium isoglycyrrhizinate liquid preparation for use in nebulizers, nebulizing for 15 min). The mice in control group 1 and the positive control group were intragastrically administered with the corresponding drugs (0.1 ml/10 g), the mice in control group 2 and the drug group 1 were aerosolizing administered with a nebulizer for 30 min, while the mice in drug group 2 were 15 min. The administration frequency was once a day for 6 consecutive days. Before the 6th administration, the mice were starved for 16-18 hours, only allowed for drinking water. After 30 minutes of administration, i.p. 1% phenol red physiological in saline solution 0.2 ml/10 g was injected and 30 minutes later, the mice were killed by cervical dislocation. After waiting for a while until the blood in the mice coagulated, the neck skin thereof was cut without obvious bleeding (to avoid the phenol red in the blood mixed into the lavage), the trachea was separated, intubated (6 # syringe needle with a smooth tip was inserted into trachea for about 3 mm from laryngeal, fixed by silk thread ligation) and connected with the syringe, and then 0.6 ml of 5% $NaHCO_3$ was slowly injected into the trachea, then gently sucked out, repeated 3 times, and 3 portions of lavage fluid were combined and centrifuged at 4000 rpm for 5 min, to obtain the supernatant.

11.2 Detection Indicators and Calculation Methods Production of Phenol Red Standard Curve:

1.95 mg of phenol red was weighted and dissolved by adding 5% $NaHCO_3$ to 3.9 ml, and the obtained solution containing 0.5 mg/ml of phenol red was used as a stock solution. 0.1 ml of the stock solution was taken and added with 3.9 ml of 5% $NaHCO_3$ to achieve the concentration of 12.5 μg/ml, which was sequentially diluted to 10 μg/ml, 7.5 μg/ml, 5 μg/ml, 2.5 μg/ml, 1.25 μg/ml, and 0.625 μg/ml. The phenol red standard curve was produced by colorimetric measuring the optical density (OD) value at the wavelength of 546 nm with an enzyme-labeling instrument.

The sample OD value at a wavelength of 546 nm was measured by an enzyme-labeling instrument, and the phenol red amount in sample was calculated from the phenol red standard curve.

11.3 Experimental Results

The experimental result data was expressed in the form of $\bar{X}\pm S$, and the statistical significance was expressed with a P value of less than 0.05. Among them, each drug group was compared with the control group 2, $^{\Delta\Delta}p<0.01$. The experimental results were shown in Table 6. The phenol red excretion amount of drug group 2 (0.2 mg/ml of magnesium isoglycyrrhizinate liquid preparation for use in nebulizers, nebulizing for 15 min) was significantly increased compared with control group 2.

TABLE 6

Effect of magnesium isoglycyrrhizinate inhaled preparation on tracheal secretion in mice $\bar{X} \pm S$)

| Group | dose | Method of administration | Number of animals | Amount of phenol red excretion (μg/ml) |
|---|---|---|---|---|
| Control group 1 (NS) | — | i.g. 6 d | 9 | 0.3962 ± 0.1715 |
| Control group 2 (NS) | — | aerosolizing inhalation 30 min*6 d | 10 | 0.3723 ± 0.1801 |
| Positive control group (ammonium chloride) | 1.0 g/kg/d*6 d | i.g. 6 d | 9 | 0.5924 ± 0.3781 |
| Drug group 1 | About 6 mg/kg/d*6 d | aerosolizing inhalation 30 min*6 d | 7 | 0.5381 ± 0.2307 |
| Drug group 2 | About 6 mg/kg/d*6 d | aerosolizing inhalation 15 min*6 d | 10 | 0.6926 ± 0.1792$^{\Delta\Delta}$ |

What is claimed is:

1. A method for alleviating phlegm by administrating an inhaled preparation of magnesium isoglycyrrhizinate to a subject in need thereof, characterized in that the inhaled preparation delivers the magnesium isoglycyrrhizinate to lungs to exert a local or systemic effect,
    wherein the inhaled preparation is a liquid preparation for use in a nebulizer or powder fir inhalation,
    wherein the liquid preparation for use in a nebulizer comprising magnesium isoglycyrrhizinate, sodium chloride, ammonium hydroxide, and water for injection, with the pH of 6.5-7.0, the nebulizer being a continuous nebulizer or a quantitative nebulizer, the amount of the magnesium isoglycyrrhizinate being from 0.1 mg/ml to 5 mg/ml, and the amount of the sodium chloride being 9 mg/ml;
    wherein the powder for inhalation comprises magnesium isoglycyrrhizinate and one or more pharmaceutically acceptable carriers, the magnesium isoglycyrrhizinate being micronized and has a particle size of 0.5-10 μm, and the pharmaceutically acceptable carrier being ground lactose, sieved lactose or a mixture of sieved lactose and fine lactose, the particle size distribution of the ground lactose ranging from 1 to 350 μm, the particle size distribution of the sieved lactose ranging from 1 to 200 μm and the article size distribution of the time lactose ranges being from 1 to 60 μm, the ground lactose having a particle size distribution of $X_{50}$ being 30-110 μm, the sieve lactose having a particle size distribution of $X_{50}$ being 35-115 μm, and the fine lactose having a particle size distribution of $X_{90}<45$ μm.

2. The method according to claim 1, characterized in that the amount of the magnesium isoglycyrrhizinate is from 0.1 mg/ml to 2.5 mg/ml.

3. The method according to claim 1, characterized in that the inhaled preparation is packaged in a single dose in a package size of 1 ml, 2 ml or 5 ml.

4. The method according to claim 1, characterized in that the magnesium isoglycyrrhizinate has a particle size of 0.5-5 μm.

5. The method according to claim 1, characterized in that the micronized magnesium isoglycyrrhizinate and the carrier are mixed and filled into a capsule or a blister.

6. The method according to claim 5, characterized in that each capsule or blister comprises 1-50 mg of micronized magnesium isoglycyrrhizinate and 0-50 mg of lactose.

7. The method according to claim 5, characterized in that each capsule or blister comprises 1-30 mg of micronized magnesium isoglycyrrhizinate and 1-40 mg of lactose.

8. The method according to claim 1, characterized in that the powder for inhalation further comprises: one or more pharmaceutically acceptable additives selected from the group consisting of surfactants, lubricants and flavoring agents.

9. The method according to claim 8, characterized in that the pharmaceutically acceptable additive is magnesium stearate and/or phospholipid.

10. The method according to claim 1, characterized in that the administration frequency of the inhaled preparation to a subject is selected from: up to three limes a day, up to twice a day, up to once a day and up to once every other day.

* * * * *

UNITED STATES PATENT AND TRADEMARK OFFICE
CERTIFICATE OF CORRECTION

PATENT NO. : 11,534,398 B2
APPLICATION NO. : 16/988289
DATED : December 27, 2022
INVENTOR(S) : Gu et al.

It is certified that error appears in the above-identified patent and that said Letters Patent is hereby corrected as shown below:

In the Claims

At Column 27, Line 58 (Claim 1), please delete "powder fir inhalation" and insert --powder for inhalation-- therefor.

At Column 28, Line 10 (Claim 1), please delete "from 1 to 200 μm and the article size distribution" and insert --from 1 to 200 μm, and the particle size distribution-- therefor.

At Column 28, Line 11 (Claim 1), please delete "time lactose ranges" and insert --fine lactose ranges-- therefor.

At Column 28, Line 13 (Claim 1), please delete "the sieve lactose" and insert --the sieved lactose-- therefor.

At Column 28, Line 64 (Claim 10), please delete "three limes a day" and insert --three times a day-- therefor.

Signed and Sealed this
Fourth Day of April, 2023

Katherine Kelly Vidal
*Director of the United States Patent and Trademark Office*